(12) United States Patent
Minato

(10) Patent No.: US 10,191,620 B2
(45) Date of Patent: Jan. 29, 2019

(54) SAMPLE-ANALYZING SYSTEM

(71) Applicant: SHIMADZU CORPORATION, Kyoto-shi, Kyoto (JP)

(72) Inventor: Hiroyuki Minato, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 410 days.

(21) Appl. No.: 14/913,746

(22) PCT Filed: Jul. 29, 2014

(86) PCT No.: PCT/JP2014/069964
§ 371 (c)(1),
(2) Date: Feb. 23, 2016

(87) PCT Pub. No.: WO2015/029676
PCT Pub. Date: Mar. 5, 2015

(65) Prior Publication Data
US 2016/0202854 A1 Jul. 14, 2016

(30) Foreign Application Priority Data
Aug. 30, 2013 (JP) .................. 2013-179181

(51) Int. Cl.
*G01N 30/24* (2006.01)
*G06F 3/0482* (2013.01)
(Continued)

(52) U.S. Cl.
CPC ........... *G06F 3/0482* (2013.01); *G01N 30/24* (2013.01); *G06F 3/04842* (2013.01);
(Continued)

(58) Field of Classification Search
CPC .. G06F 3/0482; G06F 3/04842; G06F 17/245; G06F 17/27; G01N 30/24;
(Continued)

(56) References Cited

U.S. PATENT DOCUMENTS
2013/0333490 A1  12/2013  Tanoue

FOREIGN PATENT DOCUMENTS
CN  103370626 A  10/2013
JP  9-325096 A  12/1997
(Continued)

OTHER PUBLICATIONS

Written Opinion dated Nov. 11, 2014, issued in counterpart application No. PCT/JP2014/069964, with English translation. (12 pages).
(Continued)

*Primary Examiner* — Robert R Raevis
(74) *Attorney, Agent, or Firm* — Westerman, Hattori, Daniels & Adrian, LLP

(57) ABSTRACT

In a sample-analyzing system including an analyzer (10) for analyzing a sample, an auto-sampler (20) for sequentially introducing a plurality of samples into the analyzer (10), and a controller (40) for controlling operations of the analyzer (10) and the auto-sampler (20), the auto-sampler (20) is provided with a sample rack holder (24) for holding a sample rack (21) having a plurality of wells (22) in which sample containers (23) are to be set and a sample rack imager (27) for taking, directly from above or obliquely from above, an image of the sample rack (21) held in the sample rack holder (24), whereby an incorrect input of the position information of the sample container (e.g. the well number or rack number) into an analysis schedule table is prevented.

6 Claims, 10 Drawing Sheets

(51) Int. Cl.
*G06F 3/0484* (2013.01)
*G06F 17/24* (2006.01)
*G06F 17/27* (2006.01)
*G01N 35/00* (2006.01)
*G01N 35/04* (2006.01)

(52) U.S. Cl.
CPC ............ *G06F 17/245* (2013.01); *G06F 17/27* (2013.01); *G01N 2035/0093* (2013.01); *G01N 2035/0493* (2013.01)

(58) Field of Classification Search
CPC ....... G01N 2035/0093; G01N 35/0095; G01N 2035/0493
USPC ............ 73/863, 61.55, 61.59, 64.56, 863.01, 73/864.21, 864.81, 864.85–864.87; 422/63, 64, 67, 70, 81; 436/174, 180
See application file for complete search history.

(56) References Cited

FOREIGN PATENT DOCUMENTS

| | | |
|---|---|---|
| JP | 2000-93786 A | 4/2000 |
| JP | 2003-50242 A | 2/2003 |
| JP | 2005-257548 A | 9/2005 |
| JP | 2006-71571 A | 3/2006 |
| JP | 2007-3241 A | 1/2007 |
| JP | 2011-185826 A | 9/2011 |
| JP | 2012-132694 A | 7/2012 |
| JP | 2013-11481 A | 1/2013 |
| WO | 2012/117844 A1 | 9/2012 |

OTHER PUBLICATIONS

International Search Report dated Nov. 11, 2014, issued in counterpart International Application No. PCT/JP2014/069964 (2 pages).

| ANALYSIS NO. | RACK NO. | WELL NO. | INJECTION AMOUNT (μL) | METHOD-FILE NAME | DATA-FILE NAME | ... |
|---|---|---|---|---|---|---|
| 1 | | | | | | |
| 2 | | | | | | |
| 3 | | | | | | |
| ⋮ | | | | | | |

| ANALYSIS NO. | RACK NO. | WELL NO. | INJECTION AMOUNT ($\mu$L) | METHOD-FILE NAME | DATA-FILE NAME | ... |
|---|---|---|---|---|---|---|
| 1 | 1 | 1 | 10 | METHOD 1 | DATA 1 | ... |
| 2 | 1 | 9 | 10 | METHOD 2 | DATA 2 | ... |
| 3 | 1 | 16 | 10 | METHOD 3 | DATA 3 | ... |
| 4 | 1 | 22 | 10 | METHOD 3 | DATA 4 | ... |
| 5 | 1 | 46 | 10 | METHOD 3 | DATA 5 | ... |
| 6 | 1 | 54 | 10 | METHOD 3 | DATA 6 | ... |
| 7 | 2 | 11 | 10 | METHOD 3 | DATA 7 | ... |
| 8 | 2 | 14 | 10 | METHOD 3 | DATA 8 | ... |
| ⋮ | ⋮ | ⋮ | ⋮ | ⋮ | ⋮ | |

SAMPLE-ANALYZING SYSTEM

TECHNICAL FIELD

The present invention relates to a sample-analyzing system including an analyzer for analyzing a sample, and an auto-sampler for automatically and sequentially collecting samples from a plurality of sample containers as well as for introducing those samples into the analyzer.

BACKGROUND ART

For example, in the case of automatically analyzing a plurality of samples using a liquid chromatograph, an auto-sampler is used in order to sequentially introduce those samples into the liquid chromatograph. The auto-sampler contains one or more sample racks each of which has a plurality of wells (holes with a closed bottom) for holding sample containers (e.g. vials). From each of the sample containers set in those wells, the auto-sampler collects a predetermined amount of sample in a previously specified order and injects it into a mobile-phase passage in the liquid chromatograph.

A liquid chromatograph provided with such an auto-sampler has a controller connected to it, which consists of a workstation, personal computer or similar device with a predetermined control program installed. By this controller, the operation of the auto-sampler as well as those of the various units constituting the liquid chromatograph (the liquid-sending pump, column oven, detector, etc.) are controlled.

The control process by the controller is performed according to a schedule table called the "analysis schedule table" which specifies the analyzing procedure (for example, see Patent Literature 1). FIG. 13 shows one example of the analysis schedule table. In this table, one row corresponds to one analysis, with each row describing the items of information that are necessary for performing the analysis, such as the analysis number indicative of the execution order of the analysis, the rack number indicative of the number of the sample rack in which a sample to be analyzed is set, the well number indicative of the position of the sample to be analyzed on the sample rack, the amount of sample to be injected into the liquid chromatograph, the method-file name (the name of the file in which the analyzing conditions to be applied in the analysis are described), and the data-file name (the name of the file in which the result of the analysis is to be saved). As the well number to be written in this table for indicating the well which holds the sample to be used in the analysis, serial numbers are assigned to the wells on the sample rack (e.g. in the case of a 54-hole rack, from 1 to 54).

CITATION LIST

Patent Literature

Patent Literature 1: JP 2011-185826 A

SUMMARY OF INVENTION

Technical Problem

When an analysis of a sample using such a sample-analyzing system is performed, the user initially places a sample rack carrying a plurality of samples into the auto-sampler and subsequently enters necessary information in the analysis schedule table using a monitor and input devices provided for the controller. The rack number and well number are manually entered by the user using a keyboard or similar device.

In this task, it is necessary to confirm that the rack number and well number of the sample rack on which the sample container is actually set agree with the rack number and well number entered in the analysis schedule table. However, in practice, users may possibly input an incorrect rack number or well number into the analysis schedule table, in which case the intended analysis will not be performed.

The present invention has been developed in view of the previously described point. Its objective is to provide a sample-analyzing system capable of preventing an incorrect input of the position information of the sample container (e.g. the well number or rack number) into the analysis schedule table.

Solution to Problem

The sample-analyzing system according to the present invention developed for solving the previously described problem is a sample-analyzing system including an analyzer for analyzing a sample, an auto-sampler for sequentially introducing a plurality of samples into the analyzer, and a controller for controlling operations of the analyzer and the auto-sampler, wherein the auto-sampler includes:
  a) a sample rack holder for holding a sample rack provided with a plurality of wells in which sample containers are to be set; and
  b) a sample rack imager for taking, directly from above or obliquely from above, an image of the sample rack held in the sample rack holder.

In a preferable mode of the sample-analyzing system, the controller is configured to control the operations of the auto-sampler and the analyzer according to a previously set analysis schedule table so as to make the analyzer sequentially perform a plurality of analyses, and the controller further includes:
  c) an image displayer for displaying the image taken with the sample rack imager on a monitor;
  d) an input receiver for allowing users to input the identifier of each of the wells on the sample rack in which the sample containers to be used in the respective analyses are set; and
  e) a user-input information registerer for registering, in the analysis schedule table, the identifier of each of the wells received via the input receiver, as the position information of the sample container to be used in each analysis.

As the identifier of the well, for example, the previously mentioned well number can be used. In the case where the sample rack holder can hold a plurality of sample racks, the sample-analyzing system should preferably be configured so that the input receiver allows users to input, in addition to the identifier of the well, an identifier of the sample rack in which the well concerned is provided, and the user-input information registerer registers, in the analysis schedule table, the identifier of the well and the identifier of the sample rack as the position information of the sample container to be used in each analysis.

In another mode of the sample-analyzing system, the controller is configured to control the operations of the auto-sampler and the analyzer according to a previously set analysis schedule table so as to make the analyzer sequentially perform a plurality of analyses, and the controller further includes:

f) an image displayer for displaying the image taken with the sample rack imager on a monitor;

g) a graphic displayer for displaying a plurality of graphics corresponding to the position of the wells on the sample rack by superposing the graphics on the image or placing the graphics next to the image on the monitor;

h) a selection receiver for allowing users to select, among the plurality of graphics, the graphics corresponding to the wells in which the sample containers to be used in the respective analyses are set; and i) a user-selected information registerer for registering, in the analysis schedule table, the identifier of each of the wells corresponding to the graphics selected via the selection receiver as the position information of the sample container to be used in each analysis.

Once again, in the case where the sample rack holder can hold a plurality of sample racks, the user-selected information registerer should preferably be configured to register, in the analysis schedule table, the identifier of the well corresponding to the graphic selected by the user and the identifier of the sample rack in which the well concerned is provided, as the position information of the sample container to be used in each analysis.

In still another mode of the sample-analyzing system, the controller is configured to control the operations of the auto-sampler and the analyzer according to a previously set analysis schedule table so as to make the analyzer sequentially perform a plurality of analyses, and the controller further includes:

j) a sample position locator for locating the wells in which the sample containers are set among the plurality of wells on the sample rack, by analyzing the image taken with the sample rack imager; and k) an analysis result registerer for registering, in the analysis schedule table, the identifier of each of the wells located by the sample position locator, as the position information of the sample container to be used in each analysis.

Once again, in the case where the sample rack holder can hold a plurality of sample racks, the analysis result registerer should preferably be configured to register, in the analysis schedule table, the identifier of the well located by the sample position locator and the identifier of the sample rack in which the well concerned is provided, as the position information of the sample container to be used in each analysis.

Preferably, in addition to the sample position locator and the analysis result registerer as described previously, the sample-analyzing system may further include:

l) an identification information determiner for determining identification information given to each sample container on the sample rack, by analyzing the image taken with the sample rack imager;

m) a correspondence relationship storage section for holding information about the correspondence relationship between a method file in which an analysis condition to be applied in the analyzer is described and the identification information; and n) a method registerer for finding the method file corresponding to the identification information of each of the sample containers determined by the identification information determiner, by referring to the correspondence relationship storage section for that identification information, and for registering, in the analysis schedule table, the identifier of the found method file as the file to be used in the analysis of the sample contained in the sample container.

In this case, for example, the color and/or shape of the sample container or that of the lid attached to the sample container can be used as the identification information. It is also possible to provide the sample container or its lid with a number, letter or similar code and use this code as the identification information.

Advantageous Effects of the Invention

The sample-analyzing system according to the present invention having the previously described configuration can take an image of the sample rack held in the auto-sampler by using the sample rack imager.

Additionally, for example, that image can be displayed on the monitor by using the image displayer so that users can visually check the position of the sample containers on the sample rack and input the position information of those sample containers (e.g. well numbers) in the process of creating an analysis schedule table. This effectively prevents an incorrect input of the position information.

Furthermore, by adopting the configuration in which the image is analyzed by the sample position locator and the identifier of the well in which the sample container is set is automatically registered in the analysis schedule table based on the result of the image analysis, the incorrect input of the position information of the sample container can be prevented more effectively, and additionally, the amount of labor for inputting task by the user can be reduced.

Furthermore, by adopting the configuration in which the image is analyzed by the identification information determiner and the identifier (e.g. file name) of the method file to be applied in each analysis is automatically registered in the analysis schedule table based on the result of the image analysis, the time and labor for creating the analysis schedule table can be even further reduced.

DESCRIPTION OF EMBODIMENTS

Modes for carrying out the present invention are hereinafter described using embodiments.

First Embodiment

Figure 1:
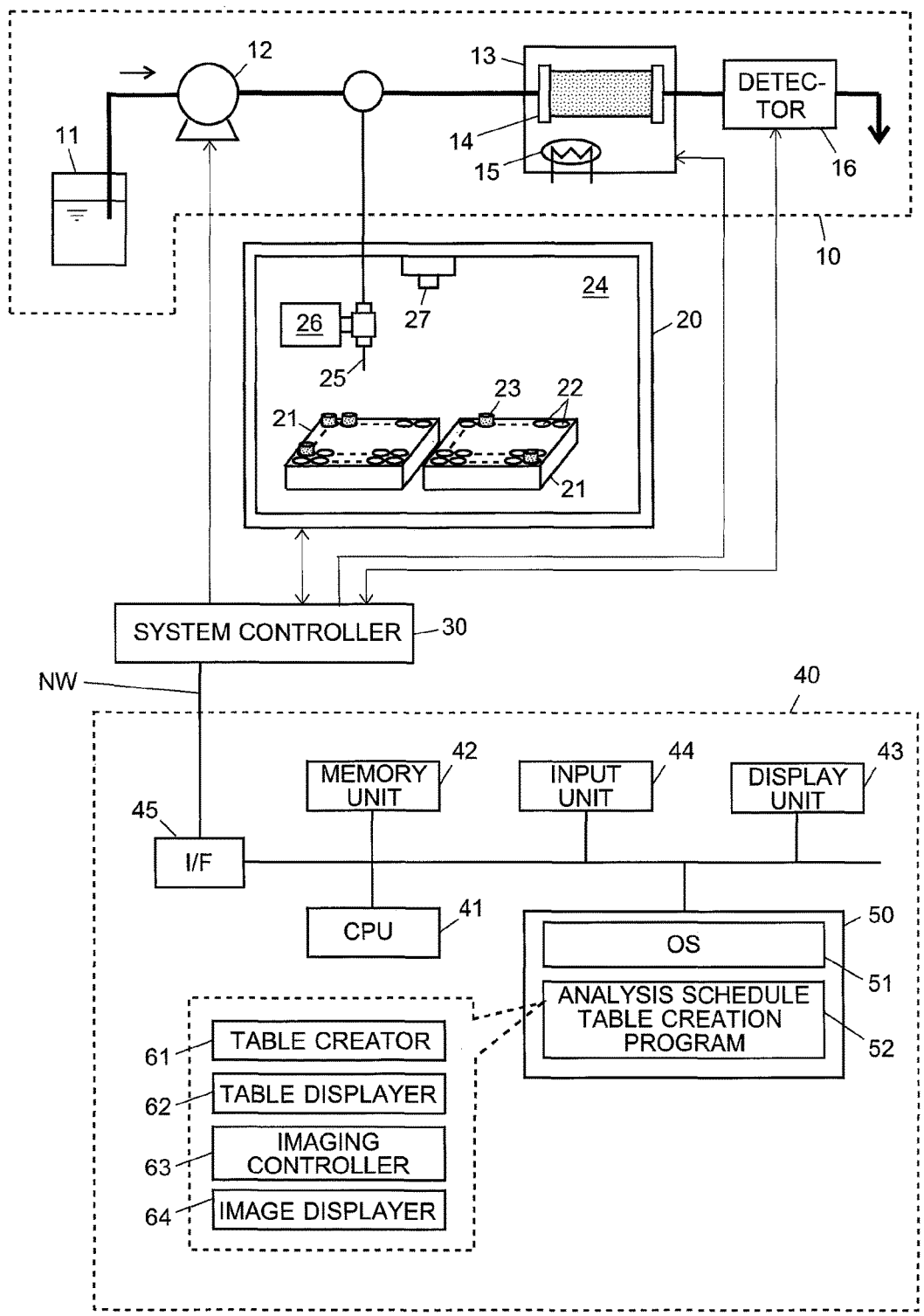
FIG. 1 is a block diagram showing the schematic configuration of a sample-analyzing system according to the first embodiment of the present invention.

FIG. 1 is a block diagram showing the schematic configuration of a sample-analyzing system according to the first embodiment of the present invention. The sample-analyzing system of the present embodiment has a liquid chromatograph 10 (which corresponds to the analyzer in the present invention), an auto-sampler 20, a system controller 30 connected to the liquid chromatograph 10 and the auto-sampler 20, as well as a main controller 40 for managing the analyzing tasks via the system controller 30 as well as for analyzing and processing the data obtained with the liquid chromatograph 10.

The liquid chromatograph 10 has a liquid-sending pump 12 for sending a mobile phase held in a mobile-phase container 11, a column oven 13 containing a column 14 along with being provided with a heater 15 for maintaining the column 14 at a predetermined temperature, as well as a detector 16 for detecting sample components sequentially eluted from the column 14.

Connected to the passage between the liquid-sending pump 12 and the column oven 13 in the liquid chromatograph 10 is an auto-sampler 20 for injecting a predetermined amount of sample into the passage. The auto-sampler 20 has a sample rack holder 24 capable of holding a plurality of sample racks 21 inside. It also has a needle 25 for suctioning a sample from a sample container 23 held in each well 22 on the sample rack 21 and a needle-driving mechanism 26 for horizontally and vertically driving the needle 25.

On the ceiling or wall surface of the sample rack holder 24, a camera 27, which is the characteristic element of the present invention (which corresponds to the sample rack imager in the present invention), is mounted. The camera 27 is a digital camera. The image taken with this camera 27 can be sent to the system controller 30 as digital data. This camera 27 is used for taking an image of the sample rack 21 from above. Therefore, a camera which is equipped with a wide angle lens or fish-eye lens having a wide angle of view should preferably be used so that the entire sample rack 21 can be captured in one image. Alternatively, the camera 27 may be arranged at a position from which the image of the sample rack 21 can be taken obliquely from above so as to include the entire sample rack 21 in one image. Alternatively, the camera 27 may be attached to the needle-driving mechanism 26 instead of the ceiling or wall surface of the sample rack holder 24. In this case, a plurality of images are taken while the needle-driving mechanism 26 is horizontally driven in the space above the sample rack 21. Those images are subsequently combined into a single image showing the entire sample rack 21.

The camera 27 should preferably be provided with a stroboscope for illuminating the sample rack 21 when taking an image. Providing an LED light or similar lighting device near the camera 27 is also possible.

The main controller 40 is actually a computer system, such as a workstation or personal computer, in which the central processing unit (CPU) 41 as the central computing processor, a memory unit 42, a monitor 43 consisting of a liquid crystal display (LCD) or similar device, an input unit 4 consisting of a keyboard, mouse and other devices, as well as a storage unit 50 consisting of a hard disk drive, solid stage drive (SSD) or similar device are connected to each other. In the storage unit 50, an operating system (OS) 51 and an analysis schedule table creation program 52 are stored. Furthermore, the main controller 40 has an interface (I/F) 45 responsible for direct connections with external devices as well as indirect connections with external devices through a local area network (LAN) or other networks. Through this interface 45, the main controller 40 is connected with the system controller 30 via a network cable NW (or wireless LAN).

In FIG. 1, a table creator 61, table displayer 62, imaging controller 63, and image displayer 64 are shown in relation to the analysis schedule table creation program 52. Basically, all of them are the functional means in the form of software modules realized by the CPU 41 executing the analysis schedule table creation program 52. The analysis schedule table creation program 52 does not need to be an independent program but can be implemented in any form; for example, it may be a built-in function of a program for controlling the liquid chromatograph 10 and the auto-sampler 20.

The image displayer 64 corresponds to the image displayer in the present invention, while the input unit 44 and the table displayer 62 correspond to the input receiver in the present invention. The table creator 61 corresponds to the user-input information registerer in the present invention.

Figures 2, 3:
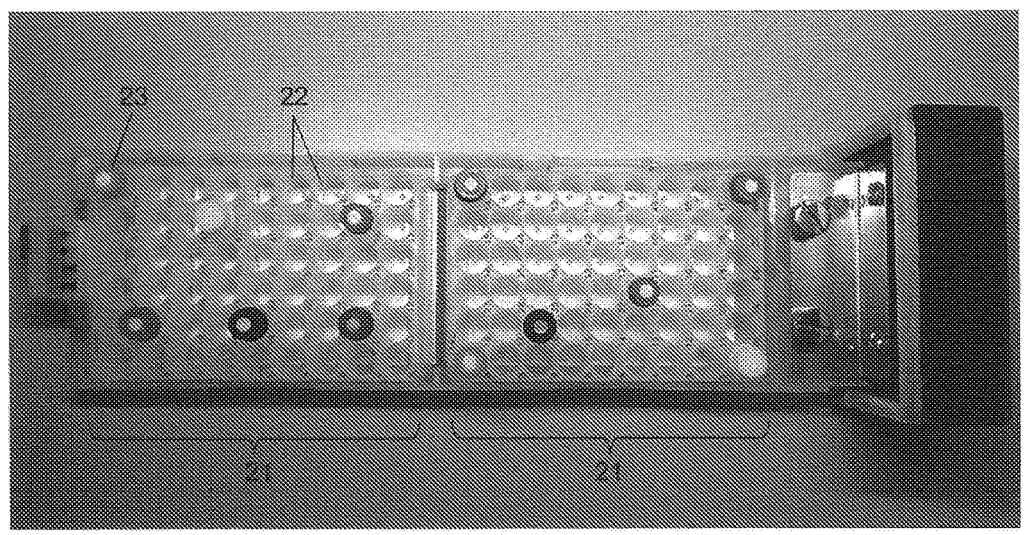
FIG. 2 is one example of the analysis schedule table displayed in the same embodiment.
FIG. 3 is one example of the image of the sample rack displayed in the same embodiment.

A sequential analysis of a plurality of samples using the sample-analyzing system according to the present embodiment is performed as follows: Initially, a user sets a sample rack 21 in the sample rack holder 24, with a plurality of sample containers 23 arranged in the rack. Subsequently, when the user enters, from the input unit 44, a command for initiating the creation of the analysis schedule table, the table creator 61 creates the analysis schedule table, and the table displayer 62 shows this analysis schedule table on the screen of the display unit 43. For example, as shown in FIG. 2, the schedule table displayed at this point is blank except for the column of the analysis number.

Subsequently, when the user performs a predetermined operation from the input unit 44, the imaging controller 63 commands the auto-sampler 20 via the system controller 30 to take an image of the sample rack 21. By this command, the operation of taking the image of the sample rack 21 with the camera 27 is performed in the auto-sampler 20. The taken image is sent to the main controller 40 as digital data. The image displayer 64 shows the image on the screen of the display unit 43. It should be noted that the operation of taking the image of the sample rack 21 does not always need to be commanded by the user as in the present example; the operation of taking and displaying the image of the sample rack 21 may be automatically performed simultaneously with the creation and display of the analysis schedule table when the creation of the analysis schedule table is commanded. As another example, the camera 27 may be directly connected to the main controller 40 so that the imaging controller 63 can command the camera 27 to take the image without any intervention by the system controller 30.

In the case of where the camera 27 is directly connected to the main controller 40, the imaging controller 63 conducts the imaging operation using the camera 27 as follows: When the user performs a predetermined operation from the input unit 44, the imaging controller 63 commands the auto-sampler 20 via the system controller 30 to prepare for the operation of taking an image of the sample rack 21. Being commanded to prepare for the imaging operation, the auto-sampler 20 performs preparatory operations necessary for the imaging operation. Specifically, it turns on the lighting within the auto-sampler, changes the position of the needle 25 (if this needle 25 interferes with the imaging operation) or drives the needle driver 26 to locate the camera 27 immediately above the sample rack 21 (if the camera 27 is attached to the needle driver 26). When the preparation for the imaging operation is completed, the auto-sampler 20 informs the main controller 40 via the system controller 30 of the completion of the preparation for the imaging operation. Upon receiving this information, the imaging controller 63 in the main controller 40 takes an image of the sample rack 21 with the camera 27. The taken image is directly sent to the main controller 40 as digital data. The image displayer 64 shows the image on the screen of the display unit 43.

Thus, an image of the sample rack 21 held in the auto-sampler 20 is simultaneously displayed with the analysis schedule table on the screen of the display unit 43. FIG. 3 shows one example of the image of the sample rack. The user visually checking this image, locates each position where the sample container 23 is set, and inputs the rack number and well number into each row of the analysis schedule table using the keyboard and other devices provided in the input unit 44. For example, if there are two 54-hole sample racks held in the sample rack holder 24, the user inputs a rack number of "1" or "2" and a well number selected from "1" through "54."

Subsequently, the user inputs other necessary items of information (i.e. the amount of injection of the sample, method-file name, data-file name, etc.) into each row of the analysis schedule table and commands the main controller 40 to initiate the analysis, whereupon the analyses described in the analysis schedule table are sequentially performed from the top row.

Figures 12, 13:
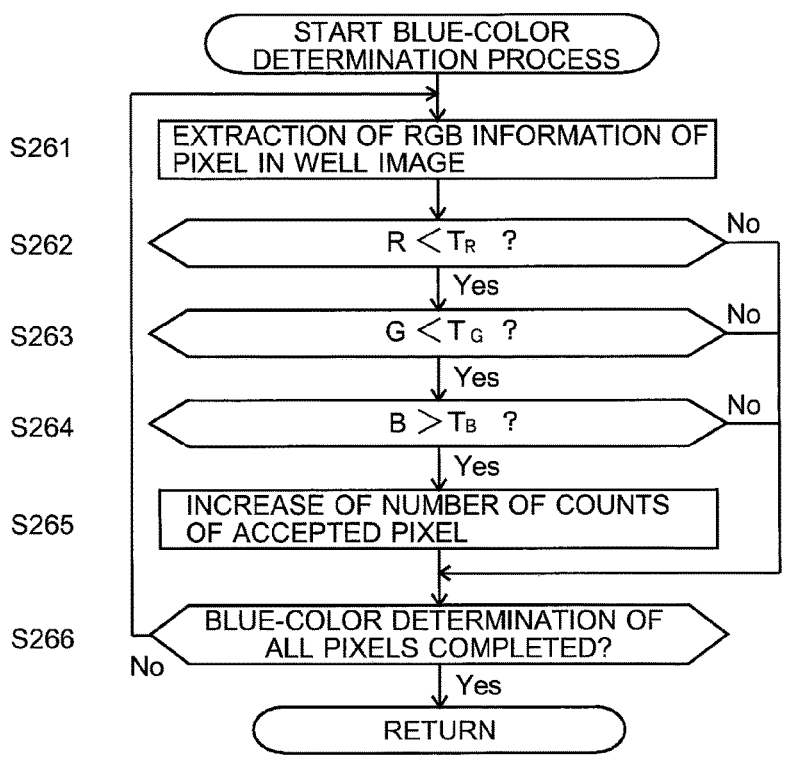
FIG. 12 is a flowchart showing the procedure of the blue-color determination process in the same embodiment.
FIG. 13 shows one example of the analysis schedule table.

For example, consider the case of performing analyses according to the analysis schedule table as shown in FIG. 13. Initially, in the auto-sampler 20, 10 μL of sample is collected through the needle 25 from the sample container set at the position identified by rack number "1" and well number "1" written in the first row (i.e. the row with analysis number "1") in the analysis schedule table, and the collected sample is injected into the liquid chromatograph 10. Subsequently, according to the analysis conditions described in the file named "METHOD 1" previously stored in the storage unit 50, the main controller 40 controls each section of the liquid chromatograph 10 to perform a chromatographic analysis of the sample. The digital detection signals produced by the detector 16 during this analysis are sent to the main controller 40 via the system controller 30. Those data are processed by the main controller 40, and the thereby obtained data of the analysis result (e.g. a chromatogram) are saved in the file named "DATA 1" in the storage unit 50. Subsequently, the analyses described in the rows with analysis numbers "2", "3", . . . are sequentially performed in a similar manner. When the analyses corresponding to all rows of the analysis schedule table are completed, the sequential analysis by the sample-analyzing system is discontinued.

Thus, in the sample-analyzing system according to the present embodiment, an image of the sample rack 21 held in the auto-sampler 20 can be taken with the camera 27 and displayed on the screen of the display unit 43. Therefore, when inputting information into the analysis schedule table, users can visually check the position of each sample container on the screen and avoid an incorrect input of the well number or rack number.

Second Embodiment

Figure 4:
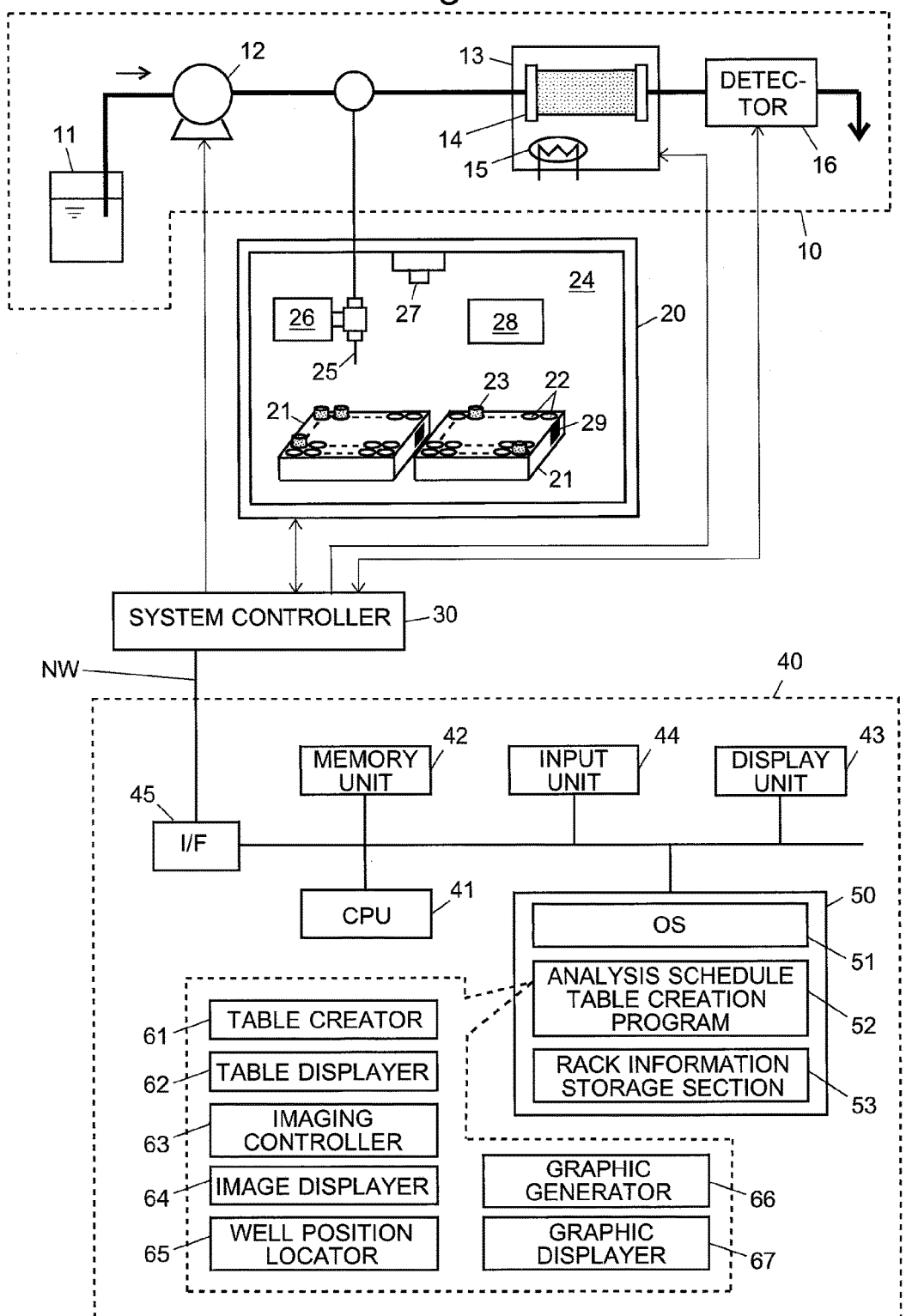
FIG. 4 is a block diagram showing the schematic configuration of a sample-analyzing system according to the second embodiment of the present invention.

FIG. 4 is a block diagram showing the configuration of a sample-analyzing system according to the second embodiment of the present invention. The components which are identical to or correspond to those of the first embodiment are denoted by the same numerals.

The sample-analyzing system according to the present embodiment has the same configuration as the first embodiment except that a rack information acquirer 28 is provided within the sample rack holder 24, a rack information storage section 53 is provided in the storage unit 50 of the main controller 40, as well as the analysis schedule table creation program 52 has a well position locator 65, graphic generator 66 and graphic displayer 67 as its functional blocks. In the present embodiment, the input unit 44 corresponds to the selection receiver in the present invention, while the table creator 61 corresponds to the user-selected information registerer.

The rack information acquirer 28 is used to obtain information on the kind and number of sample racks 21 set in the auto-sampler 20. For example, it may consist of a reader capable of reading information from a non-contact IC tag, such as RFID (radio frequency identification). In this case, an IC tag 29 in which the identification information of the sample rack 21 is previously stored is attached to the sample rack 21. The information in this IC tag 29 is read when the sample rack 21 is placed in the sample rack holder 24 or when the user enters a predetermined command using the input unit 44.

In the rack information storage section 53, the identification information stored in the IC tag 29 attached to each sample rack 21 and the information related to the arrangement of the wells on the sample rack 21 identified by that identification information are stored and linked with each other. The information related to the arrangement of the wells includes the information about the number and arrangement of the wells 22 on the sample rack 21 as well as the information about the well number assigned to each well 22. Based on the identification information of the sample rack 21 obtained by the rack information acquirer 28, the well position locator 65 reads, from the rack information storage section 53, the information related to the arrangement of the wells on the same sample rack 21. Furthermore, based on this information and the number of sample racks 21 obtained by the rack information acquirer 28, the well position locator 65 identifies the arrangement pattern of the wells within the sample rack holder 24.

Based on the arrangement pattern of the wells identified by the well position locator 65, the graphic generator 66 creates a graphic showing the positions of the wells 22 within the sample rack holder 24. For example, this graphic may consist of a plurality of circles arranged in the aforementioned arrangement pattern, with each circle representing the contour of the upper edge of the well. It is also possible to arrange a different type of figure or some characters (e.g. a number indicative of the well number of each well) according to the arrangement pattern of the wells.

Figure 5A:
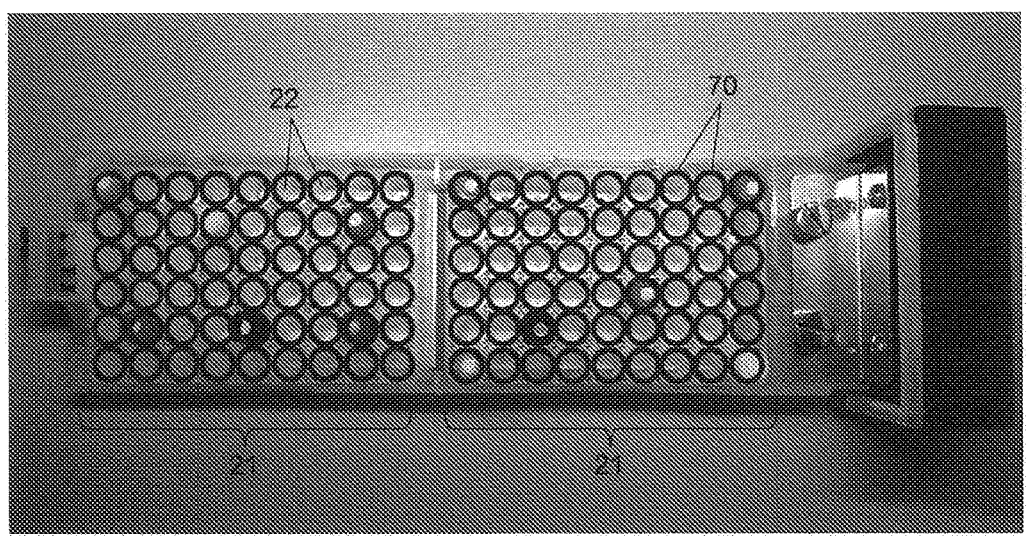
FIG. 5A is one example of the image of the sample rack and the graphic showing the well position displayed in the same embodiment.

The graphic is displayed on the screen of the display unit 43 in a superposed form on the image of the sample rack 21 by the graphic displayer 67. The image of the sample rack 21 is taken in the same way as in the first embodiment. FIG. 5A shows one example of the displayed image and graphic.

In this example, there are two 54-hole sample racks 21 placed next to each other, with each rack having the wells 22 arranged in six rows and nine columns, where one circular frame 70 is superposed on each position corresponding to one well 22 on the sample rack 21.

Figure 5B:
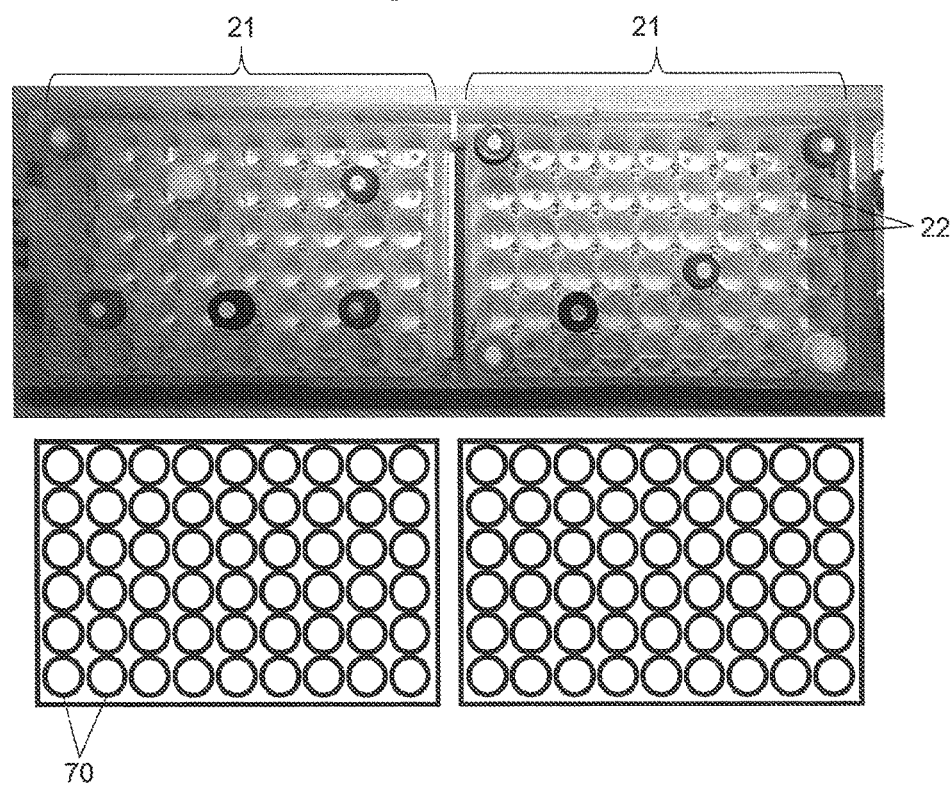
FIG. 5B is another example of the image of the sample rack and the graphic showing the well position displayed in the same embodiment.

As another example, the graphic may be displayed next to the image of the sample rack 21 on the screen of the display unit 43 by the graphic displayer 67. For instance, when the graphic is displayed next to the image as shown in FIG. 5B, the positional relationship between each well 22 and the sample container 23 can be more easily grasped than when no such display is made.

In the sample-analyzing system of the present embodiment, when the user commands the main controller 40 to initiate the creation of the analysis schedule table, the analysis schedule table as shown in FIG. 2 and an image as shown in FIG. 5A are displayed on the screen of the display unit 43. On this image, the user locates the positions of the wells in which the sample containers 23 are set on the sample rack 21, and selects the frame 70 corresponding to the first sample to be analyzed, using a mouse or similar pointing device provided in the input unit 44. Then, the table creator 61 refers to the well position locator 65 for the well number and rack number of the well 22 corresponding to the selected frame 70, and automatically registers these well and rack numbers in the first row of the analysis schedule table. In the case of FIG. 5A, for example, the rack number of the sample rack on the rear side (right side in the figure) is "1", and that of the sample rack on the front side (left side in the figure) is "2." Subsequently, as the user clicks one frame 70 after another in order of execution of the analysis, the well number and rack number of the well 22 corresponding to each frame 70 are similarly entered in each row of the analysis schedule table sequentially from the top row.

Thus, in the sample-analyzing system according to the present embodiment, when creating the analysis schedule table, the user only needs to select the desired well on the image of the sample rack displayed on the display unit 43 instead of manually inputting the well number and rack number using the keyboard. Therefore, the amount of labor for inputting the information into the analysis schedule table can be reduced, and an incorrect input of the well number or rack number can be prevented more effectively.

In the previously described example, the IC tag 29 is attached to the sample rack 21 and read by the rack information acquirer 28 consisting of an IC tag reader. There are other possible forms. For example, it is possible to provide the sample rack 21 with one or more portions each of which has a three-dimensional shape representing the rack information, and acquire this information by reading those portions with one or more photo sensors. It is also possible to attach a barcode to the sample rack 21 and read it with a rack information acquirer 28 consisting of a barcode reader. Another possible method for obtaining the information related to the kind and number of sample racks 21 is to apply a two-dimensional code to the sample rack 21, or apply an identifier simply showing numbers and/or characters representing the kind of sample rack, and to take an image of the code or identifier with the camera 27. In this case, the camera 27 doubles as the rack information acquirer 28.

It is also possible to identify the arrangement pattern of the wells on the sample rack 21 by analyzing the image of the sample rack 21 taken with the camera 27 without obtaining the rack information.

Third Embodiment

Figure 6:
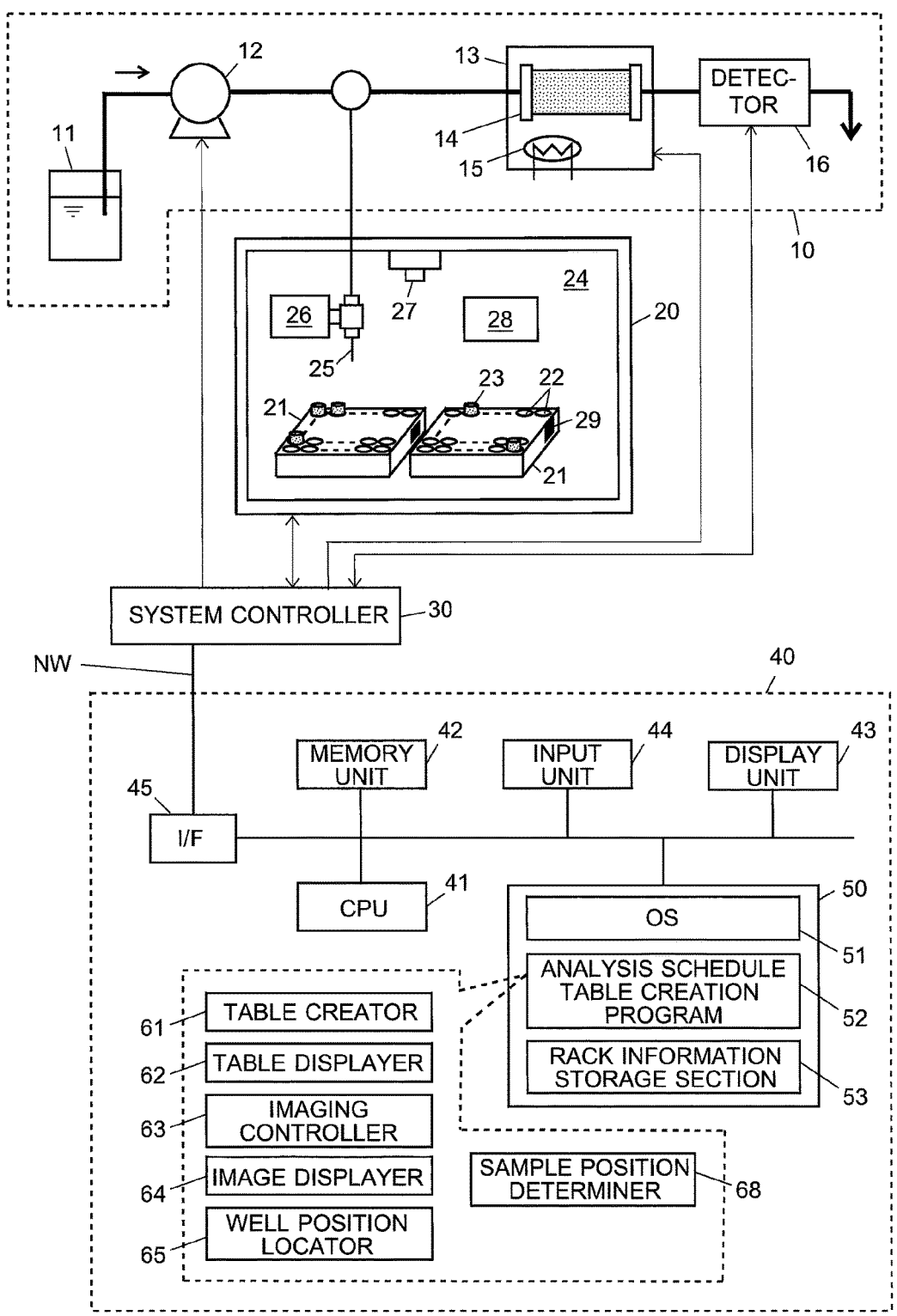
FIG. 6 is a block diagram showing the schematic configuration of a sample-analyzing system according to the third embodiment of the present invention.

FIG. 6 is a block diagram showing the configuration of a sample-analyzing system according to the third embodiment of the present invention. The components which are identical to or correspond to those of the first or second embodiment are denoted by the same numerals.

The sample-analyzing system according to the present embodiment has the same configuration as the second embodiment except that the analysis schedule table creation program 52 does not have the graphic generator 66 and the graphic displayer 67, but instead has a sample position determiner 68. The sample position determiner 68 locates the positions of the wells in which the sample containers 23 are set on the sample rack 21 based on the image taken with the camera 27 of the auto-sampler 20. In the present embodiment, the sample position determiner 68 corresponds to the sample position locator in the present invention, while the table creator 61 corresponds to the analysis result registerer in the present invention.

Figure 7:
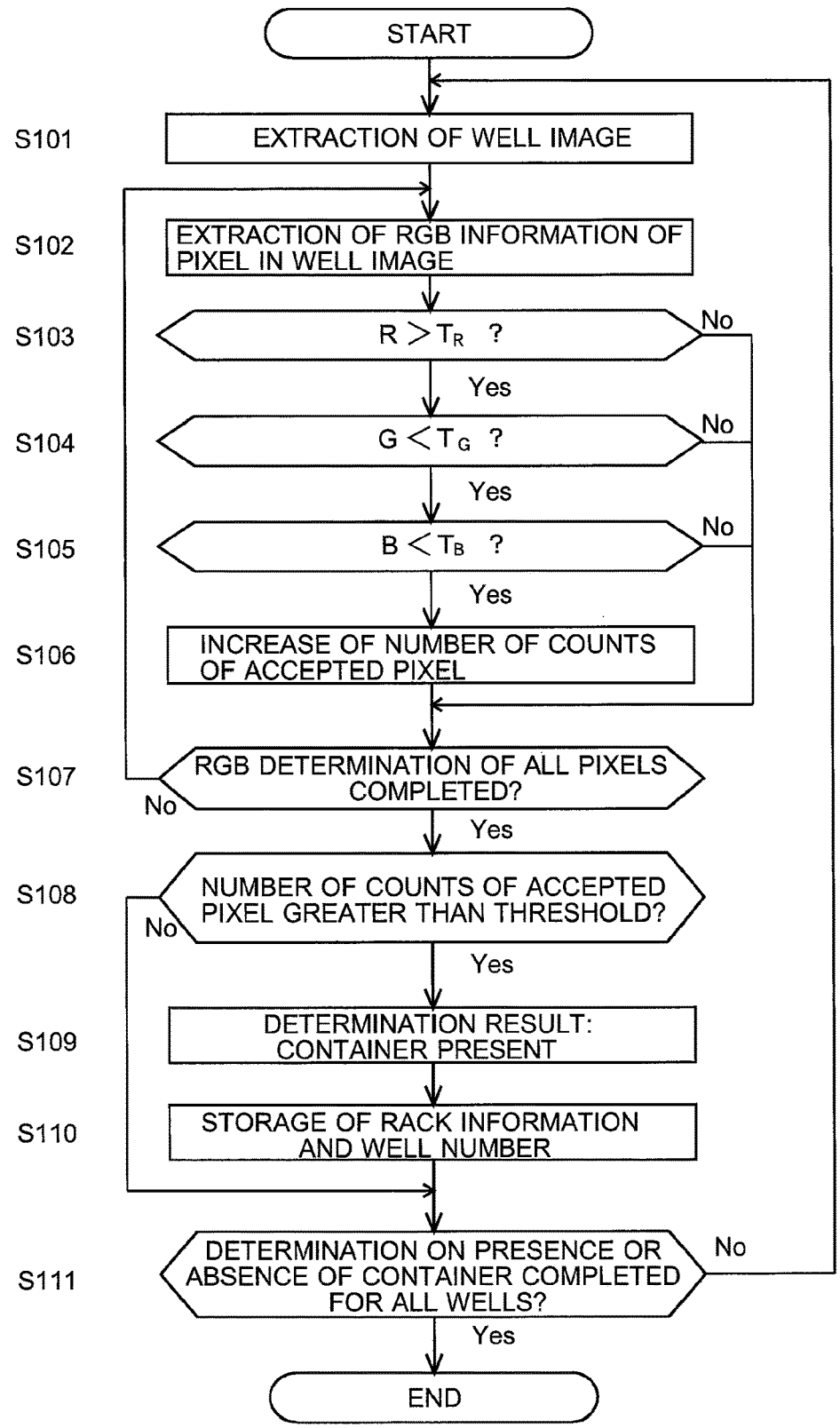
FIG. 7 is a flowchart showing the procedure performed by the sample position determiner in the same embodiment.

In the sample-analyzing system of the present embodiment, when the user, using the input unit 44, commands the main controller 40 to create the analysis schedule table, the sample position determiner 68 analyzes the image of the sample rack 21 so as to, for example, sequentially determine for each well 22, whether or not the sample container 23 is set. The procedure of this process is hereinafter described based on the flowchart of FIG. 7. It is assumed here that each sample container 23 has a red portion on its lid. For example, the red portion can be provided by using a lid which is originally red in color or a lid to which a red seal is applied.

Initially, the sample position determiner 68 obtains image data of the sample rack 21 taken with the camera 27 and retrieves, from the well position identifier 65, information related to the arrangement pattern of the wells within the auto-sampler 20 as well as the well number of each well. The image of the sample rack 21 may be automatically taken when the sample rack 21 is set in the auto-sampler 20, or it may be taken when a predetermined command is given from the input unit 44 by the user. Subsequently, image data of the area corresponding to the well identified by rack number "1" and well number "1" are extracted from the aforementioned image data (Step S101). The image of the area corresponding to a specific well extracted from the aforementioned image data in this manner is hereinafter called the "well image."

Subsequently, the sample position determiner 68 extracts RGB information from one of the pixels in the well image extracted in Step S101. The RGB information is a piece of information representing the lightness of each of the three colors of red (R), green (G) and blue (B) using 256 numbers from 0 to 255. The sample position determiner 68 examines those colors as follows: Initially, whether or not the value of R is higher than a preset threshold $T_R$ is determined (Step S103). If the value of R is higher than the threshold, whether or not the value of G is lower than a preset threshold $T_G$ is subsequently determined (Step S104). If this value is lower than the threshold, whether or not the value of B is lower than a preset threshold $T_B$ is subsequently determined (Step S105). If this value is also lower than the threshold, i.e. in the case where the value of R of the pixel is higher than its threshold while the values of G and B are lower than their respective thresholds, the pixel is considered to be an "accepted" pixel and the number of counts of the accepted pixel is increased by one (Step S106). Subsequently, whether or not the RGB determination is completed for all pixels in the well image is determined (Step S107). If the process is not completed, it returns to Step S102 to similarly perform the RGB determination on another pixel in the well image.

On the other hand, if the value of R is equal to or lower than the threshold, or if at least one of the values of G and B is found to be equal to or higher than the threshold (i.e. "No" in Step S103, S104 or S105), the process goes to Step S107 without increasing the number of counts of the accepted pixel.

When the RGB determination is completed for all pixels in the well image (i.e. "Yes" in Step S107), whether or not the number of counts of the accepted pixel on that well image has exceeded a preset threshold is determined (Step S108). If the number of counts has exceeded the threshold, it is determined that the sample container is set in the well concerned (Step S109), and the rack number and well number of that well are stored in the memory unit 42 (Step S110). Subsequently, whether or not the determination on the presence of the sample container is completed for all wells is determined (Step S111). If the determination is not completed for all wells, the process returns to Step S101.

If the number of counts of the accepted pixel is equal to or lower than the predetermined threshold (i.e. "No" in Step S108), the process goes to Step S111 without performing the step of storing the rack number and well number.

Then, the determination process is sequentially performed in a similar manner for the wells with well numbers "2", "3", . . . on the sample rack with rack number "1." When the determination on the presence or absence of the sample container is completed for all wells on the sample rack with rack number "1", the determination process is sequentially performed in a similar manner for the wells with well numbers "1", "2", "3", . . . on the sample rack with rack number "2." After the determination on the presence or absence of the sample container by the sample position locator 68 has been completed for all wells within the image (i.e. "Yes" in Step S111), the determination process by the sample position locator 68 is entirely completed.

After the determination process by the sample position locator 68 has been completed, the table creator 61 retrieves, from the memory unit 42, information of the well numbers and rack numbers of the wells for which the presence of the sample container has been determined. Among the wells for which the presence of the sample container has been determined, the wells with rack number "1" are initially registered by writing their rack numbers and well numbers in the analysis schedule table in ascending order of the well number. Subsequently, the wells with rack number "2" are similarly registered by writing their rack numbers and well numbers in the analysis schedule table in ascending order of the well number.

Thus, with the sample-analyzing system according to the present embodiment, each well in which the sample container is set on the sample rack 21 is located based on an image of the sample rack 21 taken with the camera 27, and the number of that well is automatically registered in the analysis schedule table. Therefore, the amount of labor for inputting information into the analysis schedule table can be reduced dramatically, and an incorrect input of the well number or rack number can be prevented more effectively.

In the present embodiment, the sample container is assumed to have a red portion on its lid. It is possible to use a different color. For example, a sample container having a low-lightness portion (e.g. black portion) on its lid may be used in combination with a sample rack having a high-lightness color (e.g. white), in which case the system can be configured to take a monochromatic image with the camera 27 and determine the presence or absence of the sample container based on the lightness of each pixel of the monochromatic image.

Fourth Embodiment

Figure 8:
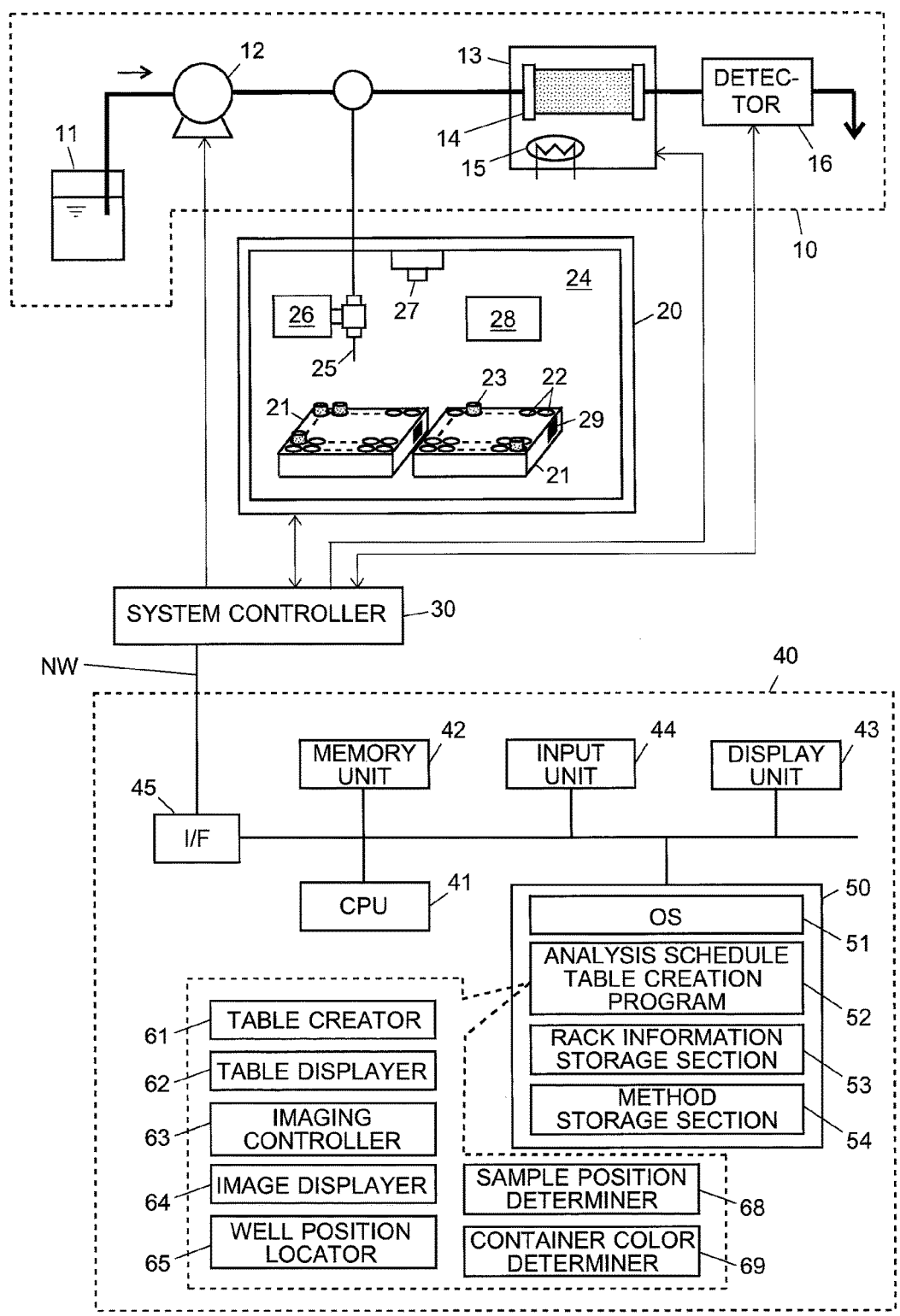
FIG. 8 is a block diagram showing the schematic configuration of a sample-analyzing system according to the fourth embodiment of the present invention.

FIG. 8 is a block diagram showing the configuration of a sample-analyzing system according to the fourth embodiment of the present invention. The sample-analyzing system of the present embodiment has the same configuration as the third embodiment except that a method storage section 54 is provided in the storage unit 50 of the main controller 40, and the analysis schedule table creation program 52 has a container color determiner 69 as a functional block.

In addition to the same functions as those of the system according to the third embodiment, the sample-analyzing system according to the present embodiment has the function of finding, for each sample, a method file to be applied to the analysis of that sample according to the lid color of the sample container holding the sample (this color is hereinafter called the "container color") and automatically registering the file name of that method file in the analysis schedule table. A method file is a file in which the operating conditions of each unit constituting the liquid chromatograph 10 are specified. Various parameters are described in this file, such as the kinds of mobile phase and column to be used in the analysis as well as the flow rate of the pump and the temperature of the column oven during the analysis.

In the method storage section 54, one or more method files prepared by users are previously stored, with one container color linked with the file name of the method file which should be applied in an analysis of a sample contained in a sample container having that container color. The container color determiner 69 determines the container color of each sample container 23 set in the sample rack 21, based on the image taken with the camera 27 of the auto-sampler 20. In the present embodiment, the container color determiner 69 corresponds to the identification information determiner in the present invention, the method storage section 54 corresponds to the correspondence relationship storage section, and the table creator 61 corresponds to the method registerer.

In the sample-analyzing system of the present embodiment, after setting the sample rack 21 in the sample rack holder 24 of the auto-sampler 20, the user enters, from the input unit 44, a command for initiating the creation of the analysis schedule table. Then, similarly to the third embodiment, an image of the sample rack 21 is taken with the camera 27. From this image, the sample position determiner 68 locates each well in which the sample container 23 is set, and the table creator 61 registers the well number and rack number of that well in the analysis schedule table.

Subsequently, the container color determiner 69 identifies the container color for each sample container 23. The process performed by the container color determiner 69 for this identification is hereinafter described using the flowchart of FIG. 9. It is assumed that each sample container has a red, green or blue portion on its lid as the identification information of the container. The task of giving such a container color is previously performed by the user by attaching one of the differently colored lids to each sample container according to the kind of sample contained in the sample container. It is also possible to apply one of the differently colored seals according to the kind of sample.

Initially, the container color determiner 69 reads, from the memory unit 42, information of the well numbers and rack numbers of the wells for which the presence of the sample container has been determined by the sample position determiner 68. From this information, the determiner 69 finds the well having the smallest well number with rack number "1" (if no such well is present, it finds the well having the smallest well number with rack number "2"). Then, the determiner 69 extracts an image of an area corresponding to that well ("well image") from the image of the sample rack (Step S210).

Figure 10:
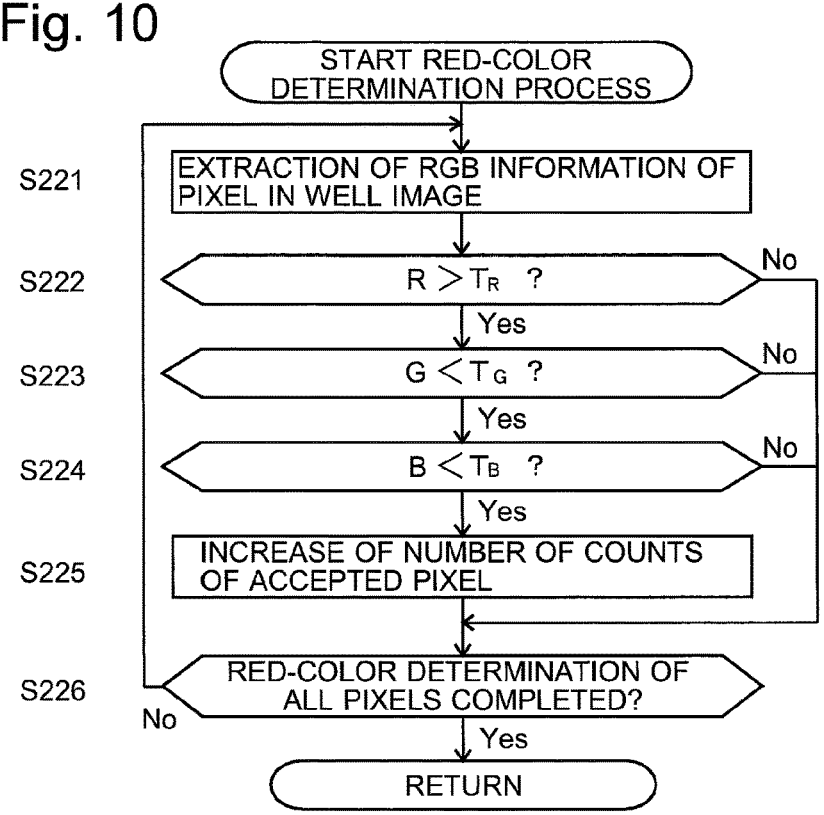
FIG. 10 is a flowchart showing the procedure of the red-color determination process in the same embodiment.

Subsequently, the container color determiner 69 performs a red-color determination process as shown in FIG. 10 for the well image (Step S220). In the red-color determination process, initially, the RGB information is extracted from one of the pixels in the well image (Step S221), and whether or not the value of R in this information is higher than a preset threshold $T_R$ is determined (Step S222). If the value of R is higher than the threshold, whether or not the value of G is lower than a preset threshold $T_G$ is subsequently determined (Step S223). If this value is lower than the threshold, whether or not the value of B is lower than a preset threshold $T_B$ is subsequently determined (Step S224). If this value is also lower than the threshold, i.e. in the case where the value of R of the pixel is higher than its threshold while the values of G and B are lower than their respective thresholds, the pixel is considered to be the accepted pixel and the number of counts of the accepted pixel is increased by one (Step S225). Subsequently, whether or not the determination of Steps S222 through S224 (red-color determination) is completed for all pixels in the well image is determined (Step S226). If the process is not completed, it returns to Step S221 to similarly perform the red-color determination on another pixel in the well image.

On the other hand, if the value of R is equal to or lower than the threshold, or if at least one of the values of G and B is found to be equal to or higher than the threshold (i.e. "No" in Step S222, S223 or S224), the process goes to Step S226 without increasing the number of counts of the accepted pixel.

Figure 9:
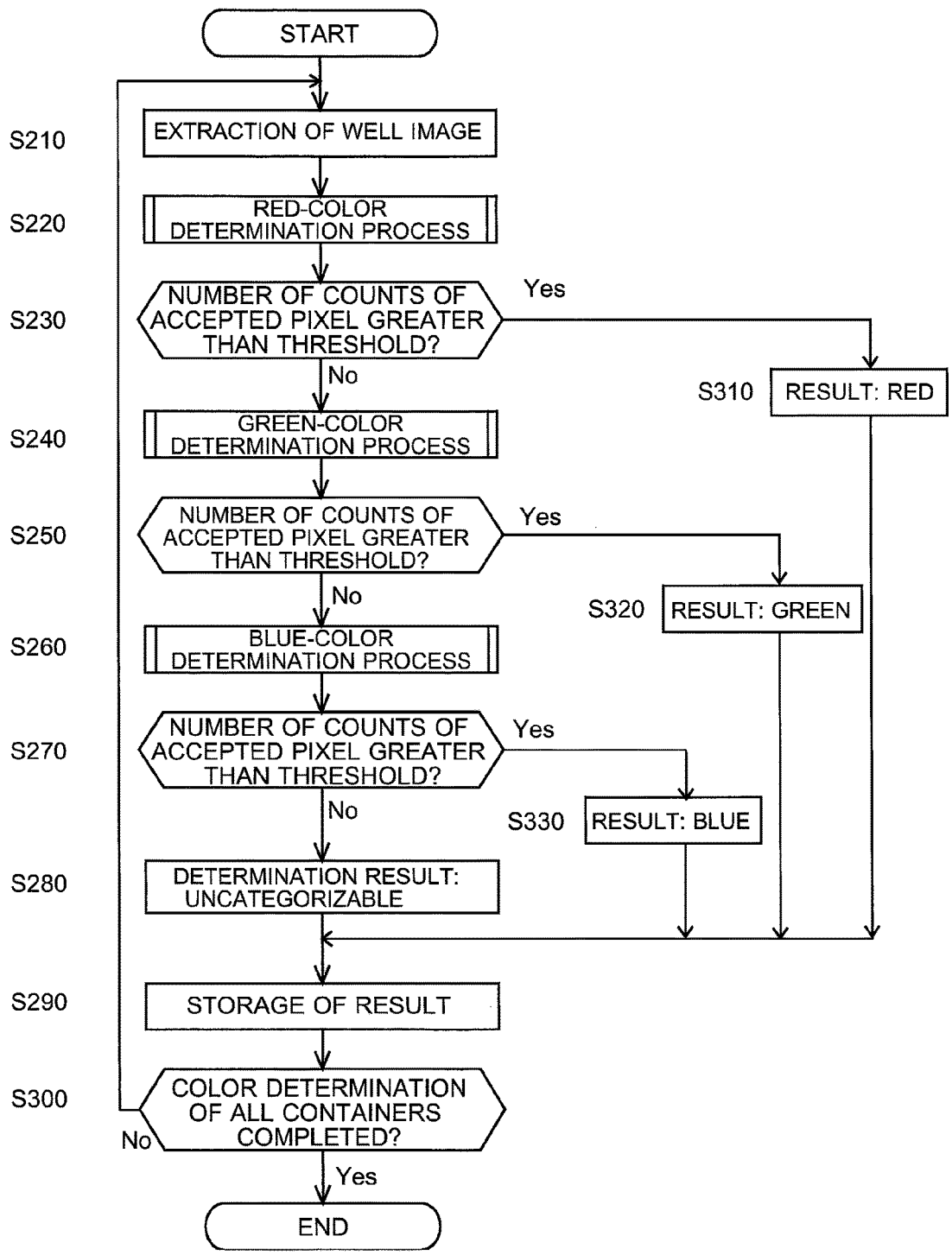
FIG. 9 is a flowchart showing the procedure performed by the container color determiner in the same embodiment.

When the red-color determination is completed for all pixels in the well image (i.e. "Yes" in Step S226), the process returns to Step S230 in FIG. 9 to determine whether or not the number of counts of the accepted pixel in the red-color determination on that well image has exceeded a preset threshold. If the number of counts has exceeded the threshold, it is determined that the red sample container is set in the well concerned (Step S310), and this determination result is stored in the memory unit 42 (Step S290).

Figure 11:
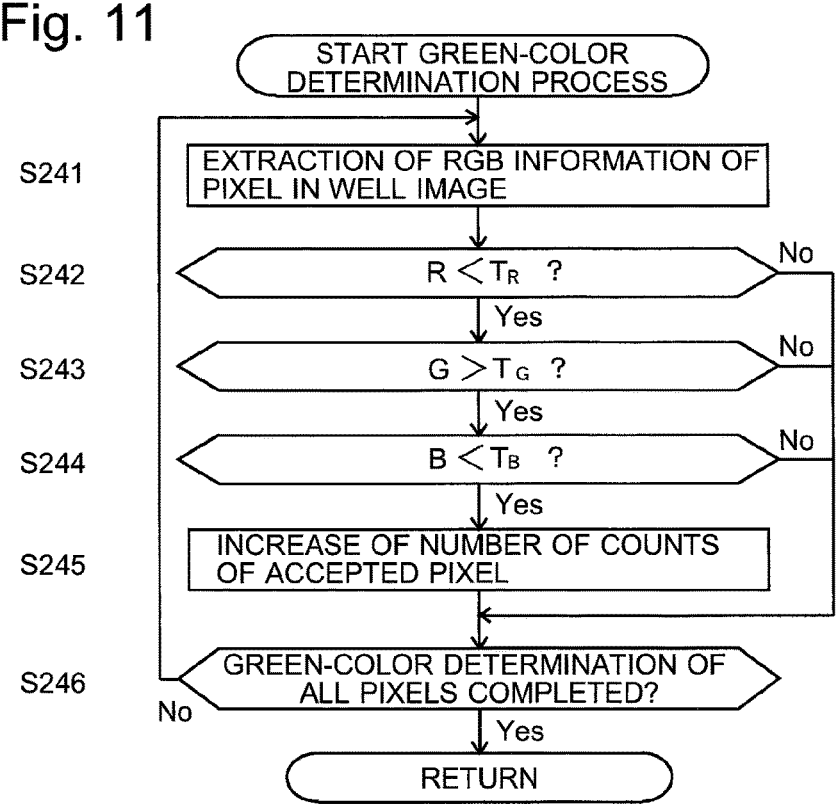
FIG. 11 is a flowchart showing the procedure of the green-color determination process in the same embodiment.

If the number of counts of the accepted pixel is equal to or lower than the preset threshold (i.e. "No" in Step S230), a green-color determination as shown in FIG. 11 is subsequently performed (Step S240). In the green-color determination, once again, the RGB information is initially extracted from one of the pixels in the well image (Step S241). Then, whether or not the value of R in this information is lower than the threshold $T_R$ is determined (Step S242). If this value is lower than the threshold, whether or not the value of G is higher than the preset threshold $T_G$ is subsequently determined (Step S243). If this value is higher than the threshold, whether or not the value of B is lower than the preset threshold $T_B$ is subsequently determined (Step S244). If this value is lower than the threshold, the pixel is considered to be the accepted pixel and the number of counts of the accepted pixel is increased by one (Step S245). Subsequently, whether or not the determination of Steps S242 through S244 (green-color determination) is completed for all pixels in the well image is determined (Step S246). If the process is not completed, it returns to Step S241 to similarly perform the green-color determination on another pixel in the well image.

On the other hand, if the value of R or B is equal to or higher than the threshold, or if the value of G has been found to be equal to or lower than the threshold (i.e. "No" in Step S242, S243 or S244), the process goes to Step S246 without increasing the number of counts of the accepted pixel.

When the green-color determination is completed for all pixels in the well image (i.e. "Yes" in Step S246), the process returns to Step S250 in FIG. 9 to determine whether or not the number of counts of the accepted pixel in the green-color determination on that well image has exceeded a preset threshold. If the number of counts has exceeded the threshold, it is determined that the green sample container is set in the well concerned (Step S320), and this determination result is stored in the memory unit 42 (Step S290).

If the number of counts of the accepted pixel is equal to or lower than the preset threshold (i.e. "No" in Step S250), a blue-color determination as shown in FIG. 12 is subsequently performed (Step S260). In the blue-color determination, once again, the RGB information is extracted from one of the pixels in the well image (Step S261). Then, whether or not the value of R in this information is lower than the threshold $T_R$ is determined (Step S262). If this value is lower than the threshold, whether or not the value of G is lower than the preset threshold $T_G$ is subsequently determined (Step S263). If this value is also lower than the threshold, whether or not the value of B is higher than the preset threshold $T_B$ is subsequently determined (Step S264). If this value is higher than the threshold, the pixel is considered to be the accepted pixel and the number of counts of the accepted pixel is increased by one (Step S265). Subsequently, whether or not the determination of Steps S262 through S264 (blue-color determination) is completed for all pixels in the well image is determined (Step S266). If this process is not completed, it returns to Step S261 to similarly perform the blue-color determination on another pixel in the well image.

On the other hand, if the value of R or G is equal to or higher than the threshold, or if the value of B has been found to be equal to or lower than the threshold (i.e. "No" in Step S262, S263 or S264), the process goes to Step S266 without increasing the number of counts of the accepted pixel.

When the blue-color determination is completed for all pixels in the well image (i.e. "Yes" in Step S266), the process returns to Step S270 in FIG. 9 to determine whether or not the number of counts of the accepted pixel in the blue-color determination on that well image has exceeded a predetermined threshold. If the number of counts has exceeded the threshold, it is determined that the blue sample container is set in the well concerned (Step S330), and this determination result is stored in the memory unit 42 (Step S290).

If the number of counts of the accepted pixel is equal to or lower than the preset threshold (i.e. "No" in Step S270), it is determined that the container color of the sample container set in the well concerned cannot be categorized in any of the red, green or blue colors (Step S280), and this determination result is stored in the memory unit 42 (Step S290).

Subsequently, whether or not the previously described process of determining the container color has been completed for all sample containers 23 held in the sample rack 21 is determined (Step S300). If the determination process for all sample containers 23 has not been completed, the process returns to Step S210.

After that, the determination process is similarly and sequentially performed for the well with the second smallest well number, the well with the third smallest well number, and so on, among the wells holding the sample containers on the sample rack with rack number "1." After the determination of the container color of all sample containers on the sample rack with rack number "1" has been completed, the determination of the container color is similarly and sequentially performed for each sample container on the sample rack with rack number "2." When the determination of the container color by the container color determiner 69 has been completed for all sample containers 23 in the sample rack holder 24 (i.e. "Yes" in Step S300), the determination process by the container color determiner 69 is entirely completed.

After the determination by the container color determiner 69 is completed, the table creator 61 retrieves, from the memory unit 42, the well number and rack number of each sample container on the sample racks as well as the determination result on the container color of each sample container. Subsequently, the table creator 61 refers to the method storage section 54 for the method-file name related to each container color, and registers that method-file name in the row identified by the aforementioned well number and rack number on the analysis schedule table (i.e. the row corresponding to the sample container concerned). For a row corresponding to the sample container whose container color has been unidentifiable, the registration of the method-file name by the table creator 61 is not performed. Instead, the user is asked to select or enter an appropriate method-file name using the input unit 44.

Thus, in the sample-analyzing system according to the present embodiment, the container color of each sample container on the sample rack is determined from an image of the sample rack, and the method file to be applied in the analysis of each sample is specified based on that container color. The file name is automatically registered in the analysis schedule table. Accordingly, the time and labor of the user in a sequential analysis of samples can be reduced dramatically.

In the present embodiment, the presence or absence of the sample container is initially determined for all wells on the sample racks by the sample position determiner 68, the well number and rack number of each sample container are registered in the analysis schedule table by the table creator 61, and subsequently, the determination by the container color determiner 69 is only performed for the wells for which the presence of the sample container has been determined. It is also possible to sequentially perform the process of determining the presence or absence of the sample container and identifying its container color for each well on the sample racks, and subsequently register the rack number, well number and method-file name by the table creator 61 after the process of determining the presence or absence of the sample container and identifying its container color is completed for all wells.

Various modes for carrying out the present invention have been described thus far using the embodiments. It should be noted that the present invention is not limited to those embodiments but can be appropriately changed within the spirit of the present invention. For example, in the previously described embodiments, two sample racks having a rectangular parallelepiped shape are set in the auto-sampler. However, the present invention can also be similarly applied in the case where the sample rack is disc shaped as well as in the case where only one sample rack or three or more sample racks are set. In the case where only one sample rack is contained in the auto-sampler, it is unnecessary to provide the analysis schedule table with the field of the rack number.

Additionally, the present invention can be applied in systems including various types of analyzers, such as a gas chromatograph or spectrophotometer, other than the sample-analyzing system including a liquid chromatograph as in the previous embodiments.

REFERENCE SIGNS LIST

10 . . . Liquid Chromatograph
20 . . . Auto-Sampler
21 . . . Sample Rack
22 . . . Well
23 . . . Sample Container
24 . . . Sample Rack Holder
27 . . . Camera
28 . . . Rack Information Acquirer
29 . . . IC Tag
30 . . . System Controller
40 . . . Main Controller
41 . . . CPU
42 . . . Memory Unit
43 . . . Display Unit
44 . . . Input Unit
50 . . . Storage Unit
52 . . . Analysis Schedule Table Creation Program
53 . . . Rack Information Storage Section
54 . . . Method Storage Section
61 . . . Table Creator
62 . . . Table Displayer
63 . . . Imaging Controller
64 . . . Image Displayer
65 . . . Well Position Locator
66 . . . Graphic Generator
67 . . . Graphic Displayer
68 . . . Sample Position Determiner
69 . . . Container Color Determiner
70 . . . Frame

The invention claimed is:

1. A sample-analyzing system including an analyzer for analyzing a sample, an auto-sampler for sequentially introducing a plurality of samples into the analyzer, and a controller for controlling operations of the analyzer and the auto-sampler, wherein the auto-sampler comprises:
   a) a sample rack holder for holding a sample rack provided with a plurality of wells in which sample containers are to be set; and
   b) a sample rack imager for taking, directly from above or obliquely from above, an image of the sample rack held in the sample rack holder;
and wherein the controller is configured to control the operations of the auto-sampler and the analyzer according to a previously set analysis schedule table so as to make the analyzer sequentially perform a plurality of analyses, the controller further comprising:
   c) an image displayer for displaying the image taken with the sample rack imager on a monitor;
   d) a graphic displayer for displaying a plurality of graphics corresponding to a position of the wells on the sample rack by superposing the graphics on the image or placing the graphics next to the image on the monitor;
   e) a selection receiver for allowing users to select, among the plurality of graphics, the graphics corresponding to the wells in which the sample containers to be used in the respective analyses are set; and
   f) a user-selected information registerer for registering, in the previously set analysis schedule table, an identifier of each of the wells corresponding to the graphics selected via the selection receiver as position information of the sample container to be used in each analysis.

2. The sample-analyzing system according to claim 1, wherein the controller further comprises:
- i) a sample position locator for locating the wells in which the sample containers are set among the plurality of wells on the sample rack, by analyzing the image taken with the sample rack imager; and
- j) an analysis result registerer for registering, in the analysis schedule table, an identifier of each of the wells located by the sample position locator, as position information of the sample container to be used in each analysis.

3. The sample-analyzing system according to claim 2, wherein the controller further comprises:
- k) an identification information determiner for determining identification information given to each sample container on the sample rack, by analyzing the image taken with the sample rack imager;
- l) a correspondence relationship storage section for holding information about a correspondence relationship between a method file in which an analysis condition to be applied in the analyzer is described and the identification information; and
- m) a method registerer for finding the method file corresponding to the identification information of each of the sample containers located by the identification information determiner, by referring to the correspondence relationship storage section for that identification information, and for registering, in the analysis schedule table, an identifier of the found method file as a file to be used in the analysis of the sample contained in the sample container.

4. A non-transitory computer readable medium that stores a program to be executed on a computer in a sample-analyzing system having an analyzer for analyzing a sample and an auto-sampler for sequentially introducing a plurality of samples into the analyzer, the auto-sampler having a sample rack holder for holding a sample rack provided with a plurality of wells in which sample containers are to be set and a sample rack imager for taking, directly from above or obliquely from above, an image of the sample rack held in the sample rack holder, the computer provided for controlling operations of the auto-sampler and the analyzer according to a previously set analysis schedule table so as to make the analyzer sequentially perform a plurality of analyses, wherein the program makes the computer function as:
- a) an image displayer for displaying the image taken with the sample rack imager on a monitor;
- b) a graphic displayer for displaying a plurality of graphics corresponding to a position of the wells on the sample rack by superposing the graphics on the image or placing the graphics next to the image on the monitor;
- c) a selection receiver for allowing users to select, among the plurality of graphics, the graphics corresponding to the wells in which the sample containers to be used in the respective analyses are set; and
- d) a user-selected information registerer for registering, in the analysis schedule table, an identifier of each of the wells corresponding to the graphics selected via the selection receiver as position information of the sample container to be used in each analysis.

5. The medium according to claim 4, wherein the program further makes the computer function as:
- g) a sample position locator for locating the wells in which the sample containers are set among the plurality of wells on the sample rack, by analyzing the image taken with the sample rack imager; and
- h) an analysis result registerer for registering, in the analysis schedule table, an identifier of each of the wells located by the sample position locator, as position information of the sample container to be used in each analysis.

6. The medium according to claim 5, characterized by further making the computer function as:
- i) an identification information determiner for determining identification information given to each sample container on the sample rack, by analyzing the image taken with the sample rack imager;
- j) a correspondence relationship storage section for holding information about a correspondence relationship between a method file in which an analysis condition to be applied in the analyzer is described and the identification information; and
- k) a method registerer for finding the method file corresponding to the identification information of each of the sample containers located by the identification information determiner, by referring to the correspondence relationship storage section for that identification information, and for registering, in the analysis schedule table, an identifier of the found method file as a file to be used in the analysis of the sample contained in the sample container.

* * * * *